(12) United States Patent
Smith et al.

(10) Patent No.: US 8,182,647 B2
(45) Date of Patent: May 22, 2012

(54) HYDROPHILIC BIODEGRADABLE ADHESIVES

(75) Inventors: Jason Smith, Pittsburgh, PA (US); Eric Beckman, Aspinwall, PA (US)

(73) Assignee: Cohera Medical, Inc., Pittsburgh, PA (US)

(*) Notice: Subject to any disclaimer, the term of this patent is extended or adjusted under 35 U.S.C. 154(b) by 538 days.

(21) Appl. No.: 12/123,927

(22) Filed: May 20, 2008

(65) Prior Publication Data

US 2009/0028812 A1    Jan. 29, 2009

Related U.S. Application Data

(63) Continuation-in-part of application No. 11/781,539, filed on Jul. 23, 2007, now abandoned.

(51) Int. Cl.
*C09J 4/00* (2006.01)

(52) U.S. Cl. .......... 156/331.7; 156/330.9; 156/331.1; 156/331.4; 424/445; 424/448; 528/48; 528/59; 528/81; 528/84; 528/85; 252/182.2; 252/182.21; 252/182.22

(58) Field of Classification Search .......... 156/60, 156/330.9, 331.1, 331.4, 331.7; 424/445, 424/448; 252/182.2, 182.21, 182.22; 523/105, 523/118; 528/59, 85, 48, 81, 84; 560/158, 560/330

See application file for complete search history.

(56) References Cited

U.S. PATENT DOCUMENTS

| | | | |
|---|---|---|---|
| 3,451,954 A * | 6/1969 | Sambeth et al. | 521/174 |
| 4,740,534 A | 4/1988 | Matsuda et al. | |
| 4,743,632 A | 5/1988 | Marinovic | |
| 4,804,691 A | 2/1989 | English et al. | |
| 4,806,614 A | 2/1989 | Matsuda et al. | |
| 4,829,099 A | 5/1989 | Fuller et al. | |
| 4,994,542 A | 2/1991 | Matsuda et al. | |
| 5,173,301 A * | 12/1992 | Itoh et al. | 424/448 |
| 5,175,229 A | 12/1992 | Braatz et al. | |
| 5,176,916 A | 1/1993 | Yamanaka et al. | |
| 5,259,835 A | 11/1993 | Clark et al. | |
| 5,266,608 A * | 11/1993 | Katz et al. | 523/111 |
| 5,374,704 A | 12/1994 | Muller et al. | |
| 5,445,597 A | 8/1995 | Clark et al. | |
| 5,457,141 A | 10/1995 | Matsuda et al. | |
| 5,486,547 A | 1/1996 | Matsuda et al. | |
| 5,496,872 A | 3/1996 | Constancis et al. | |
| 5,817,303 A | 10/1998 | Stedronsky et al. | |
| 5,855,208 A | 1/1999 | Askill et al. | |
| 5,869,593 A | 2/1999 | Helmeke et al. | |
| 5,952,422 A | 9/1999 | Chang et al. | |
| 5,981,621 A | 11/1999 | Clark et al. | |
| 6,010,714 A | 1/2000 | Leung et al. | |
| 6,033,654 A | 3/2000 | Stedronsky et al. | |
| 6,111,052 A | 8/2000 | DiDomenico et al. | |
| 6,143,352 A | 11/2000 | Clark et al. | |
| 6,146,654 A | 11/2000 | Kubo | |
| 6,177,126 B1 | 1/2001 | Hagedorn et al. | |
| 6,221,997 B1 | 4/2001 | Woodhouse et al. | |
| 6,224,630 B1 | 5/2001 | Bao et al. | |
| 6,228,969 B1 | 5/2001 | Lee et al. | |

(Continued)

*Primary Examiner* — Randy Gulakowski
*Assistant Examiner* — Michael L Leonard
(74) *Attorney, Agent, or Firm* — Fish & Richardson P.C.

(57) ABSTRACT

A moisture-curable and biodegradable adhesive that includes the reaction product of: (a) an isocyanate component having an average functionality of at least 2; (b) an active hydrogen component having an average functionality greater than 2.1; and (c) an ionic salt component having an average hydroxyl or amino functionality, or combination thereof, of at least 1.

30 Claims, 1 Drawing Sheet

Digital force gauge
Force applicator
Circular stand
Motorized test stand

U.S. PATENT DOCUMENTS

| | | |
|---|---|---|
| 6,238,687 B1 | 5/2001 | Mao et al. |
| 6,258,872 B1 | 7/2001 | Stedronsky |
| 6,306,177 B1 | 10/2001 | Felt et al. |
| 6,306,243 B1 | 10/2001 | Clark et al. |
| 6,326,025 B1 | 12/2001 | Sigler et al. |
| 6,339,130 B1 | 1/2002 | Bennett et al. |
| 6,350,463 B1 | 2/2002 | Herman et al. |
| 6,352,710 B2 | 3/2002 | Sawhney et al. |
| 6,359,100 B1 | 3/2002 | Hostettler et al. |
| 6,376,742 B1 | 4/2002 | Zdrahala et al. |
| 6,443,988 B2 | 9/2002 | Felt et al. |
| 6,524,327 B1 | 2/2003 | Spacek |
| 6,528,080 B2 | 3/2003 | Dunn et al. |
| 6,555,645 B1 | 4/2003 | Ikeda et al. |
| 6,559,350 B1 | 5/2003 | Tetreault et al. |
| 6,576,712 B2 * | 6/2003 | Feldstein et al. ............ 525/326.9 |
| 6,652,559 B1 | 11/2003 | Tetreault et al. |
| 6,653,375 B2 | 11/2003 | Moszner et al. |
| 6,703,047 B2 | 3/2004 | Sawhney et al. |
| 6,746,685 B2 | 6/2004 | Williams |
| 6,784,273 B1 | 8/2004 | Spaans et al. |
| 6,833,408 B2 | 12/2004 | Sehl et al. |
| 6,893,466 B2 | 5/2005 | Trieu |
| 6,894,140 B2 * | 5/2005 | Roby ............................. 528/70 |
| 6,960,340 B2 | 11/2005 | Rowe et al. |
| 7,044,982 B2 | 5/2006 | Milbocker |
| 7,232,454 B2 | 6/2007 | Rousseau |
| 7,264,823 B2 | 9/2007 | Beckman |
| 2006/0253094 A1 * | 11/2006 | Hadba et al. .................. 604/389 |
| 2007/0123641 A1 * | 5/2007 | Belelie et al. ................. 524/589 |
| 2007/0160569 A1 | 7/2007 | Beckman et al. |
| 2007/0190229 A1 * | 8/2007 | Beckman et al. .............. 427/2.1 |
| 2009/0246164 A1 | 10/2009 | Beckman et al. |

* cited by examiner

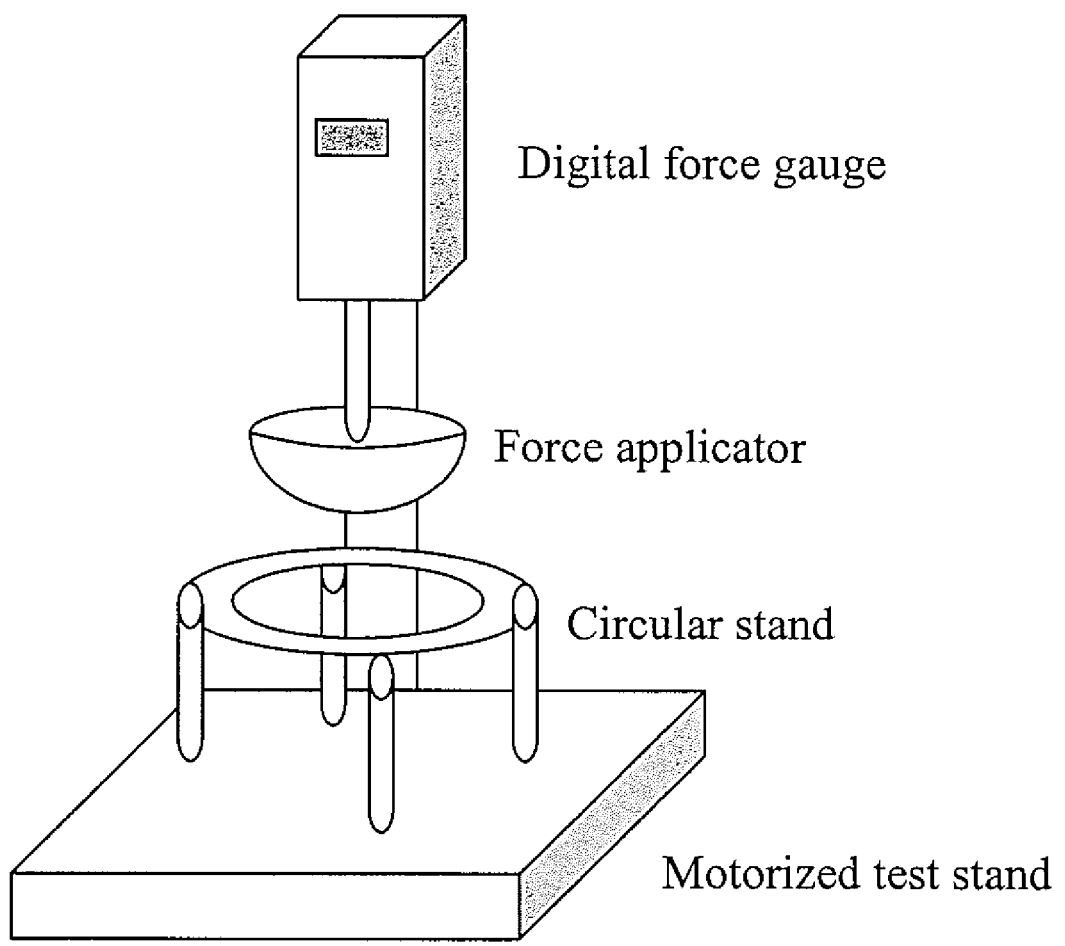

HYDROPHILIC BIODEGRADABLE ADHESIVES

STATEMENT OF RELATED CASES

This application is a continuation-in-part of Beckman et al., "Hydrophilic Biodegradable Adhesives," U.S. Ser. No. 11/781,539 filed Jul. 23, 2007, now abandoned, which is assigned to the same assignee as the present application and incorporated by reference in its entirety.

TECHNICAL FIELD

This invention relates to adhering biological tissue.

BACKGROUND

Biological and synthetic tissue adhesives have been developed as alternatives to sutures and staples for adhering biological tissue. Examples of biological tissue adhesives include fibrin glues. Examples of synthetic tissue adhesives include cyanoacrylates, urethane prepolymers, and gelatin-resorcinol-formaldehyde. Applications of adhesives to biological tissue range from soft (connective) tissue adhesion to hard (calcified) tissue adhesion. Soft tissue adhesive are used both externally and internally for wound closure and sealing. Hard tissue adhesive adhesives are used in applications that include bonding prosthetic materials to teeth and bone.

SUMMARY

An adhesive is described that includes the reaction product of: (a) an isocyanate component having an average functionality of at least 2; (b) an active hydrogen component having an average functionality greater than 2.1; and (c) an ionic salt component having an average hydroxyl or amino functionality, or combination thereof, of at least 1. The adhesive is moisture-curable and biodegradable, and may be applied to soft or hard biological tissue.

The term "component" refers to single compounds, and to blends of different compounds.

The adhesive may also include a catalyst, solvent, volatile diluent, non-volatile diluent, or combination thereof. The term "volatile" diluent refers to a diluent having a boiling point, at atmospheric pressure, of less than or equal to 40° C. Conversely, a "nonvolatile" diluent refers to a diluent having a boiling point, at atmospheric pressure, of greater than 40° C. In some embodiments, the adhesive may be provided in the form of a sprayable composition.

Inclusion of the ionic salt, which reacts with the isocyanate component of the composition and thus becomes covalently incorporated into the adhesive, increases the hydrophilicity of the adhesive relative to an adhesive that lacks the ionic salt. The increased hydrophilicity, in turn, may improve bond strength between the adhesive and biological tissue. It may also improve the solubility of other hydrophilic agents, such as hydroxyl group-containing compounds, which would further increase the overall hydrophilicity of the adhesive.

The details of one or more embodiments are set forth in the description below. Other features, objects, and advantages will be apparent from the description, drawing, and the claims.

BRIEF DESCRIPTION OF DRAWINGS

FIG. 1 is a schematic drawing of a test apparatus used to measure adhesive bond strength.

DETAILED DESCRIPTION

Adhesives suitable for application to soft and hard biological tissues are described that include the reaction product of: (a) an isocyanate component having an average functionality of at least 2; (b) an active hydrogen component having an average functionality greater than 2.1; and (c) an ionic salt component having an average hydroxyl or amino functionality, or combination thereof, of at least 1. Upon application to biological tissue in the presence of moisture, the adhesive crosslinks to form a polymer network. The crosslinked network biodegrades over time. For example, it can biodegrade in a period of time during which healing occurs. It can, for example, remain intact to adhere the tissue of a laceration or an incision until healing has sufficiently progressed such that the wound or incision remains closed. This can occur over a period of days or months, for example, depending upon the adhesive.

The isocyanate component has an average isocyanate functionality of at least 2, and may be at least 3. The term "average" reflects the fact that the multi-functional isocyanate component, as explained in the Summary, above, can include multiple types of isocyanates, including isocyanates with different functionalities. Suitable isocyanates are hydrophilic, and include those derived from amino acids and amino acid derivatives. Specific examples include lysine di-isocyanate ("LDI") and derivatives thereof (e.g., alkyl esters such as methyl or ethyl esters) and lysine tri-isocyanate ("LTI") and derivatives thereof (e.g., alkyl esters such as methyl or ethyl esters). Dipeptide derivatives can also be used. For example, lysine can be combined in a dipeptide with another amino acid (e.g., valine or glycine).

The active hydrogen component includes one or more active hydrogen reactants. The component has an average functionality greater than 2.1. Again, the term "average" reflects the fact that the active hydrogen component, as explained in the Summary, above, can include multiple types of active hydrogen reactants, including reactants with different functionalities. Some or all of the active hydrogen reactants can have an equivalent weight less than 100. The term "equivalent weight" refers to molecular weight divided by functionality. Thus, for example, glycerol, which has a molecular weight of 92 and a hydroxyl functionality "f" of 3, has an equivalent weight of approximately 31.

Examples of suitable active hydrogen components include hydroxyl-functional components, amine-functional components, thiol-functional components, carboxylic acid-functional components, and combinations thereof. In some embodiments, some or all of the functional groups may be primary groups.

One class of suitable active hydrogen components includes multi-functional alcohols selected from glycerol, di-glycerol, erythritol, pentaerythritol, xylitol, arabitol, fucitol, ribitol, sorbitol, mannitol, and combinations thereof. Also suitable are hydroxyalkyl derivatives and esters of any of these alcohols such as ethoxylated pentaerythritol.

Another class of suitable active hydrogen components includes hydroxyalkyl derivatives of $C_3$-$C_{10}$ carboxylic or dicarboxylic acids (e.g., dimethylol propionic acid, dimethylol butyric acid, and combinations thereof), and hydroxyalkyl derivatives of $C_3$-$C_{10}$ hydrocarbons (e.g., trimethylol propane).

The active hydrogen component can also be a hydroxalkyl amine (e.g., triethanolamine), a di-, tri-, or tetralkylene glycol, or combination thereof. Also suitable are hydroxyl-functional compounds selected from saccharides (e.g., glucose, fructose, sucrose, or lactose), oligosaccharides, polysaccharides, esters thereof, and combinations thereof.

The ionic salt includes one or more hydroxyl and/or amino functional groups. Consequently, it is able to react with the isocyanate-functional component of the reaction mixture, and thereby become covalently incorporated in the adhesive. Examples of suitable salts include ammoniates, halides, sulfonates, phosphonates, carboxylates, and combinations thereof. Specific examples include ammonium halides (e.g., ethyl triethanol ammonium chloride and bis(2-hydroxyethyl) dimethyl ammonium chloride), choline halides (e.g., choline chloride), and combinations thereof.

The adhesive may further include a catalyst. Examples of suitable catalysts include tertiary amines (e.g., aliphatic tertiary amines) and organometallic compounds (e.g., bismuth salts and zirconium chelates). Specific examples include 1,4-diazabicyclo[2.2.2]octane ("DABCO"), 2,2'dimorpholine diethyl ether ("DMDEE"), dibutyltin dilaurate ("DBTDL"), bismuth2-ethylhexanoate, and combinations thereof. The amount of catalyst is selected based upon the particular reactants.

The adhesive may also include a rheology modifying agent in the form of a solvent, a non-volatile diluent, and/or a volatile diluent. Examples of suitable solvents include dimethylsulfoxide (DMSO), dimethylformamide (DMF), tetrahydrofuran (THF), glyme, and combinations thereof. Examples of suitable non-volatile diluents include dimethylsulfoxide (DMSO), propylene carbonate, diglyme, polyethylene glycol diacetates, polyethylene glycol dicarbonates, dimethylisosorbide, and combinations thereof. Examples of suitable volatile diluents include hydrocarbons, perfluoroalkanes, hydrofluoroalkanes, carbon dioxide, and combinations thereof. A single reagent can perform multiple roles. Thus, for example, DMSO can function as both a solvent and a non-volatile diluent. The amount of the rheology modifying agent is selected based upon the constituents of the adhesive and the particular application for which the adhesive is being used.

The adhesives may also include one or more stabilizers. Examples include antioxidants (e.g., BHT and BHA), water scavengers (e.g., acyl and aryl halides, and anhydrides), Bronsted acids, and the like.

The adhesive cure time may be varied to meet the needs of the particular application for which the adhesive is being used. For example, cure times ranging from, e.g., about 1 minute to about 45 minutes can be achieved by combining the adhesive with an amount of an aqueous alkali solution (e.g., aqueous NaOH or KOH) just prior to application. Typically, the amount of water added to the adhesive is between 50 and 200% of the amount required to react with all free isocyanate groups in the adhesive, while the amount of base is about 100 to 200% of the amount required to neutralize acid (e.g., $H_2SO_4$) included in the adhesive preparation.

In some embodiments, the adhesive is provided in the form of a sprayable composition. Such adhesives typically have viscosities, measured at 25° C., on the order of no greater than 5000 cP (e.g., between 1 and 3000 cP).

The adhesives are useful in a variety of applications. They may be used to adhere substances to materials in the following general categories, as well as to adhere these materials to each other:

(1) soft tissue (e.g., muscle, fat, skin, fascia, tendons, and the like);

(2) hard tissue (e.g., bone, cartilage, and the like);

(3) biologically derived materials (e.g., extracellular matrices, small intestine submucosa, collage, tissue-engineered scaffolds, and the like);

(4) synthetic materials (e.g., films and meshes made of polymers such as polyester, polypropylene, and the like);

(5) metal and inorganic implants (e.g., orthopedic hardware, joint replacements, hydroxyapatite bone substitutes, and the like);

(6) tissue transplants (e.g., allografts, xenografts, autografts, and the like).

For example, the adhesives may be used in place of sutures and staples to adhere soft tissue together during surgery or as part of a wound repair protocol. Alternatively, the adhesives may be used to adhere a polymer film or mesh (e.g., a polypropylene mesh) to tissue, e.g., for the purpose of repairing soft tissue tears such as hernias. In this application, the adhesive may be formulated to cure quickly (e.g., within 5 minutes of application), e.g., by combining the adhesive with an aqueous alkali solution just prior to use. The adhesive replaces sutures and staples traditionally used to bond synthetic meshes to muscle.

The adhesive and mesh or film could be provided separately (e.g., in the form of a kit) and then combined at the time of use. For example, at the time of use, the adhesive could be applied to all or a portion of one or both sides of the mesh or film surface, and the resulting article then applied to tissue. Alternatively, the adhesive could be applied to tissue, followed by application of the mesh or film. Multiple layers of mesh or film, adhered to each other using the adhesive, may be used as well. It also would be possible to combine the adhesive and the mesh or film prior to use. For example, the adhesive could be incorporated within the mesh or film, or applied to all or a portion of one or both sides of the mesh or film surface.

EXAMPLES

Example 1

Choline Chloride (CC), Trimethylol Propane (TMP), and Ethoxylated Pentaerythritol (EP) in Dimethyl Sulfoxide (DMSO) with Bismuth2-ethylhexanoate (BIS) and Dimorpholino Diethyl Ether (DMDEE)

1.96 g TMP (14.6 mmol, —OH 43.8 mmol), 0.60 g CC (4.3 mmol, —OH 4.3 mmol), 0.46 g EP (1.7 mmol, —OH 6.8 mmol), and 7.34 g DMSO were mixed in a small glass pressure vessel at 60° C. until all components were fully dissolved. Next, 11.88 g LDI (56.0 mmol, —NCO 112.0 mmol) was added and the contents mixed at 60° C. for 30 minutes. The vessel was incubated in an ice bath for 15 minutes, followed by the addition of 33.3 mg BIS, 222 μL DMDEE, and 1.9 mg of FD&C Blue #1 dye. The vessel was mixed for 30 minutes in the ice bath, and then at room temperature for 1.5 hours. Following this, 11.1 μL sulfuric acid and 20.8 mg butyrated hydroxytoluene were added for improved shelf life and mixed for 15 minutes. The viscous liquid (~500 cP at 25° C.) was stored at room temperature. The glue was sprayed onto bovine muscle tissue using a compressed air-driven delivery device. After one minute of incubation, the tissue pieces were pressed together. After ~5-10 min the tissues were strongly held together.

Example 2

TMP, CC, and EP in DMSO and 1,1,1,3,3-pentafluoropropane (HFC-245fa) with BIS and DMDEE 1.96 g TMP (14.6 mmol, —OH 43.8 mmol), 0.60 g CC (4.3 mmol, —OH 4.3 mmol), 0.46 g EP (1.7 mmol, —OH 6.8 mmol), and 2.70 g DMSO were mixed in a small glass pressure vessel at 60° C. until all components were fully dissolved. Next, 11.88 g LDI (56.0 mmol, —NCO 112.0 mmol) was added and the contents mixed at 60° C. for 30 minutes. The closed vessel was incubated in an ice bath for 15 minutes, 9.49 g HFC-245fa was added, and the vessel mixed until homogeneous. Still on ice, 26.4 mg BIS, 176 µL DMDEE, and 1.5 mg of FD&C Blue #1 dye were added and the vessel was mixed for 30 minutes, followed by room temperature mixing for 1.5 hours. The vessel was incubated in an ice bath for 15 minutes, followed by the addition of 7.3 µL sulfuric acid and 13.7 mg butyrated hydroxytoluene for improved shelf life. The vessel was mixed for 30 minutes at room temperature and the viscous liquid was stored at 4° C. The viscous liquid (<5000 cP at 25° C.) was spread onto bovine muscle tissue, and after 1 minute of incubation the tissues were glued together.

Example 3

Xylitol and CC in DMSO and HFC-245fa with BIS and DMDEE

Xylitol and CC were mixed at a 2:1 (w/w) ratio of xylitol:CC at 70° C. until they formed a homogeneous liquid phase. The liquid was cooled and 1.50 g of the xylitol/CC mixture (Xylitol: 6.6 mmol, —OH 32.9 mmol; CC: 4.3 mmol, —OH 4.3 mmol) was combined with 7.73 g LDI (36.4 mmol, —NCO 72.9 mmol) and 2.52 g DMSO in a closed, small glass pressure vessel. The vessel was heated at 70° C. and mixed for 30 minutes. The vessel was incubated in an ice bath for 15 minutes, followed by the addition of 5.04 g HFC-245fa and mixing at room temperature for 10 minutes. The vessel was incubated on ice for 10 minutes. BIS was added in 3 aliquots totaling 35.3 mg, with 10 minutes of mixing in between additions. DMDEE (111 µL) was added at the last BIS addition. Following this, the vessel was mixed at room temperature for 1.5 hours and then stored at 4° C. The glue was spread onto bovine muscle tissue. After one minute of incubation the tissue pieces were pressed together. After ~5-10 min the tissues were strongly held together.

Example 4

TMP, CC, and EP in Propylene Carbonate (PC) and HFC-245fa with BIS and DMDEE 0.98 g TMP (7.3 mmol, —OH 21.9 mmol), 0.30 g CC (2.2 mmol, —OH 2.2 mmol), 0.23 g EP (0.9 mmol, —OH 3.4 mmol), and 2.24 g PC were mixed in a small glass pressure vessel at 70° C. until all components were fully dissolved. Next, 5.94 g LDI (28.0 mmol, —NCO 56.0 mmol) was added and the contents mixed at 70° C. for 30 minutes. The vessel was incubated in an ice bath for 15 minutes. HFC-245fa was added in two equal aliquots totaling 5.21 g, with approximately 10 minutes of mixing in between. BIS was added in 3 aliquots totaling 29.1 mg, with 10 minutes of mixing in between additions. DMDEE (97 µL) was added at the last BIS addition. Following this, the vessel was mixed at room temperature for 30 minutes and then stored at 4° C. The glue was spread onto bovine muscle tissue. After one minute of incubation the tissue pieces were pressed together. Within minutes the tissue pieces were strongly adhered.

Example 5

TMP, CC, and EP in Isosorbide Diethyl Ether (IDE) and HFC-245fa with BIS and DMDE 0.98 g TMP (7.3 mmol, —OH 21.9 mmol), 0.30 g CC (2.2 mmol, —OH 2.2 mmol), 0.23 g EP (0.9 mmol, —OH 3.4 mmol), and 2.24 g IDE were mixed in a small glass pressure vessel at 70° C. until all components were fully dissolved. Next, 5.94 g LDI (28.0 mmol, —NCO 56.0 mmol) was added and the contents mixed at 70° C. for 30 minutes. The vessel was incubated in an ice bath for 15 minutes. HFC-245fa was added in two equal aliquots totaling 5.21 g, with approximately 10 minutes of mixing in between. BIS was added in 3 aliquots totaling 29.1 mg, with 10 minutes of mixing in between additions. DMDEE (97 µL) was added at the last BIS addition. Following this, the vessel was mixed at room temperature for 30 minutes and then stored at 4° C. The glue was spread onto bovine muscle tissue. After one minute of incubation the tissue pieces were pressed together. After ~5-10 min the tissues were strongly held together.

Example 6

TMP, Xylitol, CC, and EP in DMSO and HFC-245fa with BIS and DMDEE

Xylitol and CC were mixed at a 2:1 (w/w) ratio of xylitol:CC at 70° C. until they formed a homogeneous liquid phase. The liquid was cooled and 0.38 g of the xylitol/CC mixture (Xylitol: 1.6 mmol, —OH 8.2 mmol; CC: 0.9 mmol, —OH 0.9 mmol) was combined with 1.14 g TMP (8.5 mmol, —OH 25.5 mmol), 7.27 g LDI (34.3 mmol, —NCO 68.5 mmol), and 0.74 g DMSO were mixed in a small glass pressure vessel at 60° C. for 30 minutes. The vessel was incubated in an ice bath for 15 minutes, 5.14 g HFC-245fa was added, and the vessel mixed at room temperature for 20 minutes. The vessel was incubated on ice for 10 minutes. BIS was added in 3 aliquots totaling 28.5 mg, with 10 minutes of mixing in between additions. DMDEE (90 µL) was added at the last BIS addition. Following this, the vessel was mixed at room temperature for 30 minutes and then stored at 4° C. The glue was spread onto bovine muscle tissue, and after one minute of incubation the tissue pieces were pressed together. Within minutes the tissues were strongly adhered to one another.

Example 7

Glycerol, Xylitol, and CC in DMSO and HFC-245fa with BIS and DMDEE 0.77 g glycerol (8.4 mmol, —OH 25.1 mmol), 0.55 g xylitol (3.6 mmol, —OH 18.1 mmol), 0.27 g CC (1.9 mmol, —OH 1.9 mmol), 9.60 g LDI (45.2 mmol, —NCO 90.5 mmol), and 1.87 g DMSO were mixed in a small glass pressure vessel at 70° C. for 30 minutes. The vessel was incubated in an ice bath for 15 minutes, 5.64 g HFC-245fa was added, and the vessel mixed on ice until homogeneous. Following this, 32.9 mg of BIS and 89 µL DMDEE were added. The vessel was stirred on ice for 1 hour and then stored at 4° C. The glue was spread onto bovine muscle tissue. After one minute of incubation the tissue pieces were pressed together. Within minutes the tissues were strongly adhered to one another.

Example 8

Triethanolamine (TEA) and CC in DMSO with BIS and DMDEE 1.00 g TEA (6.7 mmol, —OH 20.1 mmol), 0.31 g CC (2.2 mmol, —OH 2.2 mmol), and 4.00 g DMSO were mixed at 70° C. in a 20 mL vial until it became a single phase. The solution was cooled to room temperature, after which 4.74 g of LDI was added. The solution was mixed for 10 minutes and then transferred to an ice bath. BIS was added in 2 equal aliquots totaling 15.1 mg, with 10 minutes of mixing in the ice bath between additions. DMDEE (50 μL) was added at the last BIS addition. The formulation was mixed in the ice bath for 10 additional minutes, followed by 40 minutes at room temperature. The viscous fluid was spread onto bovine muscle tissue. After one minute of incubation the tissue pieces were pressed together. Within 5-10 minutes the tissues were strongly adhered to one another.

Example 9

TMP and bis(hydroxyethyl)dimethyl ammonium chloride (BHDMAC) in DMSO and pentafluorobutane+heptafluoropentane (HFC-365+HFC-227) with BIS and DMDEE.

0.93 g TMP (7.3 mmol) and 0.36 g BHDMAC (2.1 mmol) were dissolved in 1.27 g DMSO at 50° C. in a 75 cc high pressure glass tube with a Teflon® screw cap. The solution was then cooled to room temperature, and 49.7 μl of a 0.1 g/ml DMSO solution of BIS was added with stirring. Next, 5.67 g of LDI methyl ester (26.75 mmol) was added, whereupon the temperature rapidly increased to 70-80° C., then decreased. After 10 minutes, an additional 24.8 μl of the BIS solution was added. Ten minutes after the last BIS addition, infra-red spectroscopy of the product showed the characteristic bands for the secondary urethane NH (3250 cm$^{-1}$), the NCO group (2245-2255 cm$^{-1}$), the amide I and II bands (1714 and 1533 cm$^{-1}$), and the LDI ester (1741 cm$^{-1}$). The product was cooled to approximately 7° C. in an ice bath, after which 4.45 g of a 93:7 mixture of HFC-365 and HFC-227 was added. The resulting mixture was then stirred magnetically until a single clear phase was achieved. Next, 82.8 μL of DMDEE was added with stirring. Finally, 128 μL of a 0.216 cc/3.79 cc solution of sulfuric acid and DMSO was added to form the adhesive.

0.5335 g of the adhesive was combined with 10.1 μl of a solution of 0.1446 g KOH in 10.7327 g DI water to cure the adhesive. The cure time was measured and determined to be 37 minutes.

Example 10

Example 9 was repeated except that 1.0095 g of the adhesive was combined with 19.1 μl of a solution of 0.2048 g KOH in 5.0878 g DI water to cure the adhesive. The cure time was measured and determined to be 13 minutes.

Example 11

Example 9 was repeated except that 0.999 g of the adhesive was combined with 18.9 μl of a solution of 0.2057 g KOH in 3.8263 g DI water to cure the adhesive. The cure time was measured and determined to be 7 minutes.

Example 12

Example 9 was repeated except that 1.099 g of the adhesive was combined with 38.1 μl of a solution of 0.2057 g KOH in 3.8263 g DI water to cure the adhesive. The cure time was measured and determined to be 1.5 minutes.

Example 13

Example 9 was repeated except that 1.0968 g of the adhesive was combined with 41.5 μl of a solution of 0.1446 g KOH in 10.7327 g DI water to cure the adhesive. The cure time was measured and determined to be 4 minutes.

Example 14

Example 9 was repeated except that 0.9979 g of the adhesive was combined with 37.7 μl of a solution of 0.0463 g KOH in 6.9065 g DI water to cure the adhesive. The cure time was measured and determined to be 7 minutes.

Example 15

A sample of flank steak was obtained from a local grocery store, from which a 12.5 cm round sample was cut with a utility knife. In the center of this sample was cut a 3-cm slit using a utility knife or scalpel. A 3 cm×5 cm sample of Prolene polypropylene mesh (Ethicon, Inc) was placed over the slit (with the 5 cm length running parallel to the slit).

At this point, approximately 2 grams of the adhesive from Example 9 was weighed into a plastic weigh boat, followed by an amount of 0.2057 g KOH/3.8263 g DI water solution equal to 19 μL/g of adhesive. The mixture was stirred for 15 seconds and then smeared around the edges of the mesh using a spatula. After 30 minutes, the strength of the bond between glue, mesh, and steak was tested as described below.

Bond strength was measured using a test apparatus featuring a Mark-10 ESM Motorized Testing Stand equipped with a digital force gauge having a 200 lb capacity. The force gauge was attached to the mobile upper housing of the test stand in a manner such that the downward force applied through a force applicator (a round rubber hemisphere measuring approximately 2 inches in diameter) could be measured. The test apparatus is shown schematically in FIG. 1.

The steak/mesh/glue assembly was placed mesh side down in a circular stand that was anchored to the bottom plate of the test stand. The circular stand provided six anchoring points around the edge of the steak piece while allowing the center portion to be freely deflected downward by the force applicator. The force applicator was moved downward at a rate of 2 in/min until at least one adhesive attached site released from the steak tissue. The force applied at this point was measured and recorded. For this experiment, a force of 25 N separated mesh from steak via rupturing the adhesive bond.

Example 16

The procedure of Example 15 was repeated using Soft Mesh from Bard, Inc. in place of the Prolene polypropylene mesh. A force of 30 N was required to separate mesh from steak via adhesive bond rupture.

Example 17

The procedure of Example 16 was repeated except that the adhesive was applied only at the four corners of the mesh. A force of 35 N was required to separate mesh from steak via adhesive bond rupture.

A number of embodiments of the invention have been described. Nevertheless, it will be understood that various modifications may be made without departing from the spirit and scope of the invention. Accordingly, other embodiments are within the scope of the following claims.

What is claimed is:
1. A tissue adhesive comprising the reaction product of:
(a) an isocyanate component having an average functionality of at least 2;

(b) an active hydrogen component having an average functionality greater than 2.1, wherein the isocyanate component is selected from the group consisting of lysine diisocyanate and derivatives thereof, lysine triisocyanate and derivatives thereof, and combinations thereof; and (c) an ionic salt component having an average hydroxyl or amino functionality, or combination thereof, of at least 1, wherein the reaction product is an isocyanate-functional ionic salt that is moisture-curable and biodegradable.

2. A tissue adhesive according to claim 1 wherein the isocyanate component has an average functionality of at least 3.

3. A tissue adhesive according to claim 1 wherein the active hydrogen component is selected from the group consisting of hydroxyl-functional components, amine-functional components, and combinations thereof.

4. A tissue adhesive according to claim 1 wherein the active hydrogen component comprises a hydroxyl-functional component.

5. A tissue adhesive according to claim 1 wherein each active hydrogen component has an equivalent weight less than 100.

6. A tissue adhesive according to claim 1 wherein the active hydrogen component consists essentially of components having primary hydroxyl groups, primary amine groups, and combinations there.

7. A tissue adhesive according to claim 1 wherein the active hydrogen component is selected from the group consisting of glycerol, di-glycerol, erythritol, pentaerythritol, xylitol, arabitol, fucitol, ribitol, sorbitol, mannitol, hydroxyalkyl derivatives thereof, esters thereof, and combinations thereof.

8. A tissue adhesive according to claim 7 wherein the active hydrogen component comprises ethoxylated pentaerythritol.

9. A tissue adhesive according to claim 1 wherein the active hydrogen component comprises a hydroxyalkyl derivative of a C3-C10 carboxylic or dicarboxylic acid.

10. A tissue adhesive according to claim 9 wherein the active hydrogen component is selected from the group consisting of dimethylol propionic acid, dimethylol butyric acid, and combinations thereof.

11. A tissue adhesive according to claim 1 wherein the active hydrogen component comprises a hydroxyalkyl derivative of a C3-C10 hydrocarbon.

12. A tissue adhesive according to claim 1 wherein the active hydrogen component comprises trimethylol propane.

13. A tissue adhesive according to claim 1 wherein the active hydrogen component comprises a hydroxyalkyl amine.

14. A tissue adhesive according to claim 13 wherein the active hydrogen component comprises triethanolamine.

15. A tissue adhesive according to claim 1 wherein the active hydrogen component comprises a di-, tri-, or tetraalkylene glycol, or combination thereof.

16. A tissue adhesive according to claim 1 wherein the active hydrogen component is selected from the group consisting of saccharides, oligosaccharides, polysaccharides, esters thereof, and combinations thereof.

17. A tissue adhesive according to claim 1 wherein the ionic salt component is selected from the group consisting of ammoniates, halides, sulfonates, phosphonates, carboxylates, and combinations thereof.

18. A tissue adhesive according to claim 1 wherein the ionic salt component comprises a choline halide.

19. A tissue adhesive according to claim 18 wherein the ionic salt component comprises choline chloride.

20. A tissue adhesive according to claim 1 wherein the ionic salt component comprises an ammonium halide.

21. A tissue adhesive according to claim 1 wherein the viscosity of the adhesive is selected such that the adhesive is sprayable.

22. A tissue adhesive according to claim 1 wherein the adhesive further comprises a catalyst.

23. A tissue adhesive according to claim 1 wherein the adhesive further comprises a solvent.

24. A tissue adhesive according to claim 23 wherein the solvent is selected from the group consisting of dimethylsulfoxide (DMSO), dimethylformamide (DMF), tetrahydrofuran (THF), glyme, and combinations thereof.

25. A tissue adhesive according to claim 1 further comprising a non-volatile diluent.

26. A tissue adhesive according to claim 25 wherein the non-volatile diluent is selected from the group consisting of dimethylsulfoxide (DMSO), propylene carbonate, diglyme, polyethylene glycol diacetates, polyethylene glycol dicarbonates, dimethylisosorbide, and combinations thereof.

27. A tissue adhesive according to claim 1 further comprising a volatile diluent.

28. A tissue adhesive according to claim 27 wherein the volatile diluent is selected from the group consisting of hydrocarbons, hydrofluoroalkanes, perfluoroalkanes, carbon dioxide, and combinations thereof.

29. A tissue adhesive according to claim 1 wherein the viscosity of the adhesive is no greater than 5000 cP.

30. A tissue adhesive according to claim 29 wherein the viscosity of the adhesive is between 1 and 3000 cP.

* * * * *